US006527868B2

(12) United States Patent
Moraly et al.

(10) Patent No.: US 6,527,868 B2
(45) Date of Patent: Mar. 4, 2003

(54) DEXTROSE IN POWDER FORM AND A PROCESS FOR THE PREPARATION THEREOF

(75) Inventors: Franck Moraly, Lestrem (FR); Erik Labergerie, Armentieres (FR); José Lis, La Gorgue (FR); Philippe Lefevre, Merville (FR)

(73) Assignee: Roquette Freres, Lestrem (FR)

(*) Notice: Subject to any disclaimer, the term of this patent is extended or adjusted under 35 U.S.C. 154(b) by 0 days.

(21) Appl. No.: 10/210,169

(22) Filed: Aug. 1, 2002

(65) Prior Publication Data

US 2003/0005923 A1 Jan. 9, 2003

Related U.S. Application Data

(62) Division of application No. 09/464,024, filed on Dec. 15, 1999, now Pat. No. 6,451,122.

(51) Int. Cl.⁷ .............................................. C13K 13/00
(52) U.S. Cl. .................... 127/63; 426/456; 426/471; 426/660; 424/441; 424/465
(58) Field of Search ...................... 127/63, 30; 426/660, 426/456, 471; 424/465, 441

(56) References Cited

U.S. PATENT DOCUMENTS

| 3,650,829 | A | * | 3/1972 | Walon ......................... 127/30 |
| 4,059,460 | A | | 11/1977 | Schollmeier et al. |
| 4,297,146 | A | * | 10/1981 | Mise et al. ................... 127/60 |
| 4,342,603 | A | * | 8/1982 | Daniels ........................ 127/30 |
| 4,357,172 | A | * | 11/1982 | Edwards ...................... 127/60 |
| 4,831,129 | A | | 5/1989 | Serpelloni |

FOREIGN PATENT DOCUMENTS

| GB | 2 077 270 | 12/1981 |
| WO | WO 94/28181 | 12/1994 |

OTHER PUBLICATIONS

Abstract in English of the Handbook Pharmaceutical Excipients, pp 149–150 "Dextrates", No date provided.
Abstrack in English of patent BE 431 954 (Feb. 1939).
Abstract in English of patent FR 1 331 252 (Aug. 1962).

* cited by examiner

*Primary Examiner*—David Brunsman
(74) *Attorney, Agent, or Firm*—Sturm & Fix LLP

(57) ABSTRACT

The invention relates to a dextrose in powder form, characterised in that it has a dextrose content at least equal to 99%, an α crystalline form content at least equal to 95%, a water content at most equal to 1% and a compressibility, determined according to a test A, at least equal to 80 N, preferably in the range 100 N and 200 N. The invention also relates to the use of said dextrose in powder form as a sweetener or excipient, particularly in food or pharmaceutical compositions, for example, for the preparation of confectionery or of tablets to be sucked, chewed, dissolved or swallowed.

4 Claims, No Drawings

DEXTROSE IN POWDER FORM AND A PROCESS FOR THE PREPARATION THEREOF

CROSS REFERENCE TO RELATED APPLICATIONS

This application is a Divisional of U.S. patent application Ser. No. 09/464,024, filed Dec. 15, 1999, now U.S. Pat. No. 6,451,122 Sep. 12, 2002 the disclosure of which is being incorporated herein by reference in its entirety.

The present invention relates to a dextrose in powder form with a high dextrose content, an essentially a crystalline form and a pronounced anhydrous nature, also having a rapid rate of dissolution in water, a particular particle size distribution and excellent flowability. The invention also relates to a dextrose in powder form of which the industrial use properties in direct compression are improved, and to a process for the preparation thereof.

Dextrose, produced industrially by hydrolysis of various starches, has been commonly used, mainly in the food industry, for numerous years.

Dextrose in powder form is used to advantage in pharmaceutical and food applications (notably in confectionery) where it is necessary to have dry products, for example, for the production of tablets or chocolate articles.

Three crystalline forms of dextrose are traditionally described, i.e. α dextrose monohydrate, anhydrous α dextrose and anhydrous β dextrose.

Although numerous processes have been proposed for directly converting glucose solutions to solid materials of any crystalline form, α dextrose monohydrate remains the virtually exclusive source of dextrose powder. This α dextrose monohydrate is traditionally produced by slow crystallisation, by cooling supersaturated syrups with a high glucose content originating from the hydrolysis of starch.

The main advantages thereof are its flowability and its low tendency to agglomerate, its chemical or physical stability during handling, its solubility in water, its whiteness and its sweet character without an abnormal taste.

However, its water content of about 9% in the form of water of crystallisation precludes its use in fields of application where problems relating to the moisture content of the finished products must be avoided.

Anhydrous crystalline α dextrose, a very pure crystalline dextrose with a low water content, was therefore chosen.

This anhydrous α dextrose is generally produced by dissolving the crystals of α dextrose monohydrate in water at temperatures from 60° C. to 65° C., for example, in autoclaves under a high vacuum and under carefully controlled operating conditions.

However, the anhydrous α dextrose thus obtained has the disadvantages of dissolving relatively slowly in water and having a tendency to cake during dissolution. In fact, a part of the anhydrous α dextrose is converted once again during this dissolution to α dextrose monohydrate which agglomerates and delays the dissolution of the anhydrous α dextrose accordingly.

In order to dissolve satisfactorily the two α monohydrate and α anhydrous forms, it is necessary, therefore, to use water at a high temperature or to add the dextrose gradually to water with stirring.

It has been proposed, therefore, to use anhydrous crystalline β dextrose which has a much better rate of dissolution compared with that of anhydrous α dextrose and even monohydrate.

However, it is well known to experts in the crystallisation of dextrose that although the transition point of the crystallisation of α dextrose monohydrate to anhydrous α dextrose is about 55° C., that of anhydrous α dextrose to anhydrous β dextrose is about 110° C.

Consequently, in order to obtain anhydrous β dextrose, it is necessary to operate at a high temperature at which dextrose is not very stable. This result limits all the more the industrial use of such a crystallisation process.

Moreover, as any dextrose in powder form composed of a single crystalline species and prepared in the traditional way is generally not very compressible, it is necessary to add maltodextrins or polysaccharides to it for the production of tablets.

However, the anhydrous products prepared in this way according to the prior art have generally been unsatisfactory because of problems of agglomeration and handling due to the maltodextrins or polysaccharides.

Patent application FR 2.398.802 describes a dextrose in powder form which has good flowability, does not agglomerate, is appreciably free from an unpleasant taste and coloured impurities but also has satisfactory compression properties.

The analysis of said dextrose in powder form reveals that it is composed of a mixture, in roughly equivalent amounts, of anhydrous α and β dextrose. The process for the preparation thereof by crystallisation and granulation is, however, particularly long and tedious.

Patent application WO 94/28.181 describes a dextrose which, apart from having a particularly low moisture content and a rapid rate of dissolution in water at ambient temperature, also has compression properties which allow it to be used for the production of tablets without the need for it to undergo special additional treatments or to add a binder.

However, the dextrose in powder form thus obtained is characterised not only by a composition containing the two anhydrous α and β crystalline forms with a high anhydrous β dextrose content of the order of 60 wt.%, but also by its amorphous nature, i.e. a degree of crystallinity only in the range 87% to 90%. Moreover, its dextrose content is only 94%, the remaining 6% being composed mainly of maltose and maltodextrins with a higher degree of polymerisation (DP).

It is apparent from the above that there is an unsatisfied need to obtain a dextrose in powder form with a high dextrose content and high crystalline purity and which also has excellent compression properties.

To its merit, the Applicant company has developed, after considerable research, a new dextrose in powder form.

The dextrose in powder form according to the invention is thus characterised initially in that it has:

a dextrose content at least equal to 99%, an α crystalline form content at least equal to 95%, a water content at most equal to 1%,
a compressibility, determined by a test A, at least equal to 80 N, preferably in the range 100 N to 200 N.

The dextrose content may be measured by a conventional high performance liquid chromatography method. It is determined here at a value at least equal to 99%.

The crystallinity is a measure of the crystalline structure or otherwise of the product. This crystallinity is determined according to measurements of the latent heat of fusion carried out using a differential calorimeter. The crystallinity of the product is determined by comparing the latent heat of fusion of the product with that of crystalline references having a variable proportion of α and β dextrose.

The degree of crystallinity for the anhydrous α form of dextrose in powder form according to the invention is determined at a value at least equal to 95%. The anhydrous β dextrose form is therefore in a small proportion, contrary to what may be found in commercial anhydrous products which nevertheless have similar compression properties.

The moisture content of the particles is also measured by traditional methods known, moreover, to the skilled person. The water content of said dextrose in powder form is thus at most equal to 1%, indicating a pronounced anhydrous character.

According to the invention the compressibility of the dextrose in powder form is determined by test A below, described in patent EP 220.103 owned by the Applicant company. This test A consists in measuring the force, expressed in newtons, which is representative of the compressibility of the dextrose in powder form studied. This force therefore reflects here the resistance to crushing of a tablet which is cylindrical with convex sides (radius of curvature 14 mm), having a diameter of 13 mm, a thickness of 6 mm and a weight of 0.764 g, i.e. an apparent density of 1.3 g/ml.

It is particularly surprising that a dextrose in powder form can simultaneously have a high dextrose content, at least equal to 99%, of which the anhydrous α crystalline form represents at least 95%, and a compressibility of at least 80 N, preferably in the range 100 N to 200 N.

In fact, it is conventionally accepted that the preparation of a dextrose in powder form having properties of high compressibility requires the mixing of α dextrose monohydrate with additives such as maltose and maltodextrins with a higher DP, or the production of mixed compositions of anhydrous α and β forms of dextrose, for example, by atomisation of a glucose syrup with a high dry matter content.

However, the dextrose in powder form according to the invention has a high compressibility, characteristic of said traditional dextrose in powder form, and a high crystalline purity of the anhydrous α form, characteristic of a crystalline dextrose with high purity and good chemical stability.

Consequently, and contrary to what was expected, it has a remarkably high compressibility for a crystalline purity never reached by the dextrose in powder form of the prior art.

By way of example, the dextrose in powder form sold under the brand names EMDEX®, UNIDEX®, ROYAL T® and CANTAB® in the field of direct compression are products in the monohydrate form. They are generally obtained by atomisation of a glucose syrup with a dextrose equivalent (DE) in the range 93% to 99%, as specified in appendix 3 of the monograph "Dextrates" of the Handbook of Pharmaceutical Excipients.

A close analysis of their composition reveals, however, in the range 5% to 6% of maltose, maltotriose and maltodextrins with a higher DP.

With regard to the dextrose in powder form sold under the name "Dry Dextrose Anhydrous SD 99" by CARGILL, which has excellent compression properties, in addition to its two anhydrous α and β crystalline forms and a little of contaminating α monohydrate form, it has an amorphous form content in the range 10% to 30%. Moreover, it does not generally comply with the monographs "Dextrates" of the Handbook of Pharmaceutical Excipients.

The dextrose in powder form according to the invention is particularly suited to the production of tablets. In fact, according to the invention the anhydrous form characteristic of the dextrose in powder form has the advantage of avoiding the marked changes in hardness and texture associated with the migration of water itself due to changes in temperature, i.e. by successive periods of heating/cooling.

The dextrose in powder form according to the invention also has a high dextrose content and purity, which also gives the tablets prepared from said dextrose in powder form a better texture for the application of tablets to be chewed, avoiding the "pasty" nature of the tablets prepared from dextrose in powder form of the prior art.

The dextrose in powder form according to the invention may also be characterised by its rapid rate of dissolution in water.

In order to measure the rate of dissolution, 5 g exactly of the product to be tested are introduced into 150 ml of demineralised and degassed water kept at 20° C. and undergoing agitation at 200 rpm.

The dissolution time corresponds to the time required, after the product has been introduced, to obtain perfect visual clarity of the suspension thus prepared.

Under these conditions, the dextrose in powder form according to the invention generally has a rate of dissolution of less than 10 s. Advantageously, it has a dissolution time of about 6 s.

These times are generally very much lower than those obtained with all the dextrose powders currently on sale.

The dextrose in powder form according to the invention may also be characterised by its apparent density and its friability.

The determination of apparent density is carried out using an instrument sold by HOSOKAWA under the brand name POWDER TESTER by applying the method recommended for measuring an apparent density.

Under these conditions, the dextrose in powder form according to the invention has a relatively low apparent density, generally in the range 0.5 g/ml to 0.7 g/ml, preferably in the range 0.55 g/ml to 0.65 g/ml.

The friability of said dextrose in powder form is determined according to a test described in the patent EP 645.096 owned by the Applicant company.

It has a value generally at least equal to 60, preferably in the range 60 to 80.

This low friability value is all the more remarkable in that the dextrose in powder form according to the invention has a low density. In fact, it is conventionally accepted that a dextrose in powder form is less friable the greater its density and compressibility.

Surprisingly and unexpectedly, and contrary to what is commonly accepted, the dextrose in powder form according to the invention does not conform with the rule according to which the lower the apparent density of a dextrose in powder form the more friable it is, that is, susceptible to a deterioration in its particle size by mechanical action.

The consequence of the combined improved properties of compressibility and friability is, in particular, to make the dextrose in powder form according to the invention particularly well suited to food and pharmaceutical applications.

The high compressibility of said dextrose in powder form allows, in fact, the production by simple direct compression of tablets with great hardness (for the application of tablets to be sucked) or of tablets of moderate hardness (for the application of tablets to be crunched).

Moreover, it is also possible to characterise the dextrose in powder form according to the invention by its mean diameter and its flowability, these properties being particularly suitable for said applications in compression.

The dextrose in powder form according to the invention thus generally has a mean diameter in the range 150 μm to 200 μm. These values are determined on a LASER LS particle size analyser with the brand name COULTER®.

The flowability of the dextrose is evaluated using the POWDER TESTER instrument sold by HOSOKAWA. This instrument makes it possible to measure, under standardised and reproducible conditions, the flowability of a powder and to calculate a flow grade, also known as the Carr index. The dextrose in powder form according to the invention has an excellent flow grade, generally at least 70, preferably in the range 70 to 80. This value is generally equivalent to that of the dextrose powders of the prior art. This is particularly remarkable in that, compared with the prior products with the same flow, the dextrose in powder form according to the invention has a finer particle size.

Without wishing to be bound by any theory, it may be thought that the physical/chemical characteristics mentioned above of the dextrose in powder form according to the invention explain its excellent flowability. These characteristics relate in particular to its dextrose content, its crystalline purity, its centred particle size distribution but also the characteristic shape of its particles.

Dextrose in powder form may be obtained by carrying out a step involving the granulation of α dextrose powder having essentially the α crystalline form by the wet method using a binder, then an ageing step by drying the granular dextrose thus obtained. It should be pointed out that, as the Applicant company has observed, the product according to the invention cannot be prepared from a glucose solution by simple atomisation, crystallisation or granulation because in this case the remarkable compressibility properties can, in fact, be obtained only by the addition of additives, as pointed out above.

In order to obtain α dextrose in powder form according to the invention having the functional characteristics mentioned, the Applicant company observed that it was appropriate to choose, as the starting dextrose, a dextrose powder with a high dextrose content and having an essentially α crystalline form which can be obtained by crystallisation or atomisation.

The term "essentially a crystalline form" means a dextrose powder whose α crystalline form represents at least 95% of the crystalline forms which dextrose may take. The high dextrose content means here a value at least equal to 99%.

The particle size of said starting dextrose powder does not in itself constitute a limiting factor for producing a dextrose in powder form according to the invention.

The binder is composed of water or a glucose syrup with a dry matter content at least equal to 30%, preferably in the range 40% to 80%. As the proportion of dry matter provided by the binder gives at most 63% of the anhydrous β form and 37% of the anhydrous α form during the recrystallisation thereof, the glucose concentration of the binder is chosen such as to keep the level of the anhydrous β form of the final product at a value below 5%.

Surprisingly and unexpectedly, the Applicant company observed that the granulation of a dextrose powder by the wet method using a binder makes it possible to prepare, with a high yield, a product according to the invention in terms of its hygroscopic properties, its density, particle size distribution and flowability. In fact, the processes described earlier do not make it possible to obtain all the desired characteristics.

In order to carry out granulation, it is possible to use, for example, a continuous mixer-granulator of the vertical FLEXOMIX type sold by SCHUGI, or of the horizontal CB type sold by LÖDIGE into which the starting dextrose powder to be granulated is introduced continuously by way of a weight feeder, and the binder (water or a glucose syrup) is introduced continuously by way of a volumetric feeder.

Granulation may also be carried out in an atomisation tower or in a fluidised bed granulator. In a first preferred embodiment of the process for the preparation of a sorbitol in powder form according to the invention, a continuous mixer-granulator of the SCHUGI vertical FLEXOMIX type is chosen to be used. The starting dextrose powder and the binder are very intimately mixed in the mixer-granulator fitted with a shaft with knives arranged in the form of blades, and a system for spraying liquids by injection nozzles.

According to a preferred embodiment of the process according to the invention, good dispersion of the constituents and agglomeration of the particles of the starting dextrose powder are carried out by high speed agitation, i.e. at a value at least equal to 1500 rpm, preferably at least equal to 3000 rpm. At the outlet of the mixer-granulator, the granules formed are discharged continuously into a drier.

Discharge is carried out preferably by gravity in the case of said vertical granulator, and by pressure by way of the shaft of rotating knives if the horizontal granulator is used.

This second drying step at the outlet of the mixer-granulator makes it possible to remove the water originating from the binder and to crystallise the dry matter originating from the binder, if a glucose syrup was optionally used, such that crystallisation takes place after the prior granulation step.

Drying is carried out in two successive steps. The first step makes it possible to bring the water content of the moist granulated powder obtained at the outlet of the mixer-granulator to a value in the range 7% to 9% and the second drying step makes it possible to reduce the water content to a value at most equal to 1% so as to obtain the dextrose in powder form according to the invention.

The drier used in the first drying step may comprise, for example, a fluidised bed drier.

The drier used in the second drying step is a rotary drum or a vacuum oven as will be illustrated below.

The dextrose in powder form according to the invention is obtained after cooling and optionally sieving. In this case, the fine particles may be recycled directly to the start of granulation, and the coarse particles may be ground and recycled to the start of sieving or to the start of granulation.

In a second preferred embodiment of the process for the preparation of a sorbitol in powder form according to the invention, the choice is made to carry out granulation of the sorbitol powder by the wet method in an atomisation tower. In this case, the crystalline dextrose is introduced into said atomisation tower and water or a glucose syrup as defined above is introduced as binder.

The choice is made to feed an MSD (multi-stage dryer) atomisation tower with a water evaporation capacity of the order of 350 kg/h with dextrose powder at a flow rate in the range 400 kg/h to 600 kg/h, granulation taking place with water as binder, as will be illustrated below.

In view of the melting points of the various crystalline forms of sorbitol, the Applicant company found that it was necessary to monitor rigorously the operating temperatures of the atomisation tower.

It is advantageous, therefore, to adjust the temperature of the feed air to a value in the range 180° C. to 200° C., the vapour temperature to a value in the range 90° C. to 95° C. and the temperature of the static bed to a value in the range 70° C. to 80° C.

The dextrose in powder form according to the invention may be used advantageously, due to its functional properties mentioned above, as a sweetener or excipient in compositions used particularly in the food and pharmaceutical sectors. More particularly, said dextrose in powder form may be used advantageously in the confectionery sector, notably in chocolate making. Moreover, certain advantageous properties of said dextrose in powder form favour its use in applications of tablets to be sucked, chewed, dissolved, and swallowed.

Other features and advantages of the invention will become apparent on reading the examples below. They are given here, however, only by way of non-limiting example.

EXAMPLE 1

A vertical FLEXOMIX mixer-granulator from SCHUGI is fed continuously by way of a powder feeder at a flow rate of 500 kg/h with a dextrose powder produced by crystallisation. Moreover, the mixer-granulator is fed continuously with water at 65° C. and at a flow rate of 50 l/h by way of a spray nozzle. The rotating knife shaft is adjusted beforehand to a speed of 3000 rpm.

The moist granulated powder with a water content equal to 14% obtained at the outlet of the mixer-granulator falls continuously by gravity into a SCHUGI fluidised bed drier with two compartments. In the first compartment, the granulated product is dried by air at 120° C. then cooled with air at 20° C. in the second compartment such that its water content is reduced to 8.5%. The product thus obtained is then dried in a rotary drum with air at 120° C. and cooled to 20° C. such that its final water content is reduced to 0.5%. The granulated, dried and cooled product is then sieved continuously over a rotary screen fitted with two wire meshes of 120 μm and 600 μm. The starting dextrose powder A and the dextrose in powder form B thus obtained and according to the invention have the characteristics summarised in Table I below.

TABLE I

| Parameters | A | B |
|---|---|---|
| Dextrose content (wt. %) | 99.5 | 99.5 |
| α Crystalline form content (%) | 98 | 98 |
| Water content (%) | 8.9 | 0.5 |
| Rate of dissolution in water (s) | <6 | 6 |
| Apparent density (g/ml) | 0.5 | 0.61 |
| Mean diameter (μm) | 60 | 170 |
| Flow grade (value/100) | 43 | 72 |
| Compressibility (N) | <50 | 136 |
| Friability (%) | nd | 69 |

EXAMPLE 2

A vertical FLEXOMIX mixer-granulator from SCHUGI is fed continuously in the same way as in example 1.

The moist granulated powder with a water content equal to 9% at the outlet of the mixer-granulator falls continuously by gravity into a SCHUGI fluidised bed drier with two compartments.

In the first compartment, the granulated product is dried with air at 12° C. then cooled with air at 20° C. in the second compartment such that its water content is reduced to 7%.

It is then dried in a vacuum oven at a temperature of 105° C. under a pressure of 80 millibars and cooled to a temperature of 20° C. such that its final water content is reduced to 0.5%.

The granulated, dried and cooled product is then sieved continuously over a rotary screen fitted with two wire meshes of 120 μm and 600 μm.

The starting dextrose powder C and the dextrose in powder form D thus obtained according to the invention have the characteristics summarised in table II below.

TABLE II

| Parameters | C | D |
|---|---|---|
| Dextrose content (wt. %) | 99.5 | 99.5 |
| α Crystalline form content (%) | 98 | 98 |
| Water content (%) | 0 | 0.5 |
| Rate of dissolution in water (s) | >6 | 6 |
| Apparent density (g/ml) | 0.53 | 0.6 |
| Mean diameter (μm) | 60 | 170 |
| Flow grade (value/100) | 43 | 75 |
| Compressibility (N) | >50 | 147 |
| Friability (%) | >50 | 70 |

EXAMPLE 3

The process is carried out with the same starting dextrose powder A which was used in example 1.

An MSD atomisation tower with an evaporation capacity of 350 kg/h is fed with sorbitol powder A in a quantity of 460 kg/h.

Granulation with water is carried out by spraying water in a quantity of 100 l/h through a nozzle at a pressure of 45 bar.

The drying air enters at 230° C. and leaves at 83° C. and the temperature of the vapours is determined at 95° C. The static bed at the bottom of the tower is cooled with air at 74° C.

At the outlet of the atomisation tower, the product passes over a vibrated fluidised bed where it is cooled by air in three temperature zones fixed at 40° C., 20° C. and 20° C. respectively.

The starting product A and the product thus obtained E have the characteristics summarised in table III below.

TABLE III

| Parameters | A | E |
|---|---|---|
| Dextrose content (wt. %) | 99.5 | 99.5 |
| α Crystalline form content (%) | 98 | 98 |
| Water content (%) | 8.9 | 0.5 |
| Rate of dissolution in water (s) | <6 | 6 |
| Apparent density (g/ml) | 0.5 | 0.62 |
| Mean diameter (μm) | 60 | 180 |
| Flow grade (value/100) | 43 | 70 |
| Compressibility (N) | <50 | 140 |
| Friability (%) | nd | 70 |

EXAMPLE 4

Other products in powder form according to the invention are prepared by applying the processes described in examples 1 to 3, but by modifying the granulation conditions so as to obtain a range of samples.

The products obtained have the characteristics set out in table IV below and are compared with the dextrose in powder form known elsewhere.

TABLE IV

| Parameters | Products according to the invention | Anhydrous CERELOSE ® | Dry Dextrose Anhydrous SD 99 |
|---|---|---|---|
| Dextrose content (wt. %) | >99 | 95 | 98 |
| Maltose content (%) | 0 | 0.2 | 1.2 |
| Maltotriose content (%) | 0 | 0.1 | 0.1 |
| α Crystalline form content (%) | 95–100 | 96 | 67 |
| Water content (%) | <1 | 0.2 | 1 |
| α Monohydrate form content (%) | 0 | 0 | 3 |
| Rate of dissolution in water (s) | <10 | 27 | 22 |
| Apparent density (g/ml) | 0.55–0.65 | 0.78 | 0.65 |
| Mean diameter (μm) | 150–200 | 150–250 | 450–550 |
| Flow grade (value/100) | 70-80 | 62 | 77 |
| Compressibility (N) | 100-200 | 0 | 122 |
| Friability (%) | 60–80 | 45 | 58 |

The dextrose products in powder form according to the invention, unlike the products of the prior art, all have excellent functional properties in terms of their flowability, rate of dissolution, compressibility and friability, and this with high dextrose contents and high crystalline purity of the anhydrous a form, making them suitable for use without disadvantage in the food and pharmaceutical industries.

EXAMPLE 5

Plain chocolate bars containing or not containing the dextrose in powder form B according to the invention prepared according to example 1 are produced by following the formulation given in table V below.

TABLE V

| Ingredients | Bar (a) | Bar (b) |
|---|---|---|
| Sucrdse | 467 g | 267 g |
| Dextrose in powder form B | — | 200 g |
| Cocoa liquor with 54% fatty matter | 450 g | 450 g |
| Cocoa butter | 80 g | 80 g |
| Soya lecithin | 3 g | 3 g |
| TOTAL | 1000 g | 1000 g |

The method of producing these bars involves:

heat-treating all the raw materials at 45° C. over a water bath, mixing the sweetening materials and the cocoa liquor in a KENWOOD planetary mixer, grinding said mixture in a GRENIER-CHARVET three-cylinder grinder in 3 passes at 20 bars, adding cocoa butter to this ground mixture, conching in a double jacket bowl thermostated to 80° C., provided with a paste and driven by a HEIDOLPH engine unit, for 24 h at 80° C., adding soya lecithin 1 h prior to the end of conching, heat treating at 28.5° C. and moulding in the form of bars.

A sensory analysis is carried out in order to determine the parameters of sweet flavour and texture in the mouth of the plain chocolate bars thus obtained.

The results show that the incorporation of 20% of the anhydrous dextrose in powder form in this formulation of plain chocolate bars instead of sucrose does not alter their organoleptic properties.

The texture in the mouth is identical to that of the chocolate bars produced with sucrose. Similarly, no difference in viscosity is observed between these chocolate bars.

The dextrose in powder form according to the invention is thus well suited to this application in chocolate making.

What is claimed is:

1. A process for the preparation of a dextrose in powder form having:

a dextrose content at least equal to 99%, an α crystalline form content at least equal to 95%, a water content at most equal to 1%, a compressibility, determined according to test A, at least equal to 80 N, said test A consisting in measuring the strength, expressed in Newton, which is necessary to cause a tablet prepared from said dextrose to be crushed, this strength thus reflecting the resistance to crushing of said tablet, which is cylindrical with convex sides (radius of curvature 14 mm), having a diameter of 13 mm, a thickness of 6 mm and a weight of 0.764 g, i.e. an apparent density of 1.3 g/ml, the said strength being exerted against the peripheral surface of the tablet in the direction of the axis of revolution thereofby means of a mechanical movable stop applied against the said surface along a generatrix, the said tablet being furthermore immobilized against the mechanical stationary stop also applied against the peripheral surface of the tablet along a generatrix, the latter being diametrically opposed to the generatrix against which the mechanical movable stop is applied, the process comprising the steps of:
granulation of a dextrose powder essentially in the alpha crystalline form using a binder; and
ageing by drying the granulated dextrose thus obtained.

2. The process of claim 1, wherein the granulation step is carried out in a continuous mixer-granulator.

3. The process of claim 1, wherein the granulation step is carried out in an atomization tower.

4. In a process wherein dextrose is an ingredient for the manufacture of an element selected from the group consisting of a sweetener, an excipient, a confectionary, a chocolate confectionary, a tablet to suck, a tablet to dissolve, and a tablet to swallow, the improvement comprising selecting the dextrose in powder form having:

a dextrose content at least equal to 99%, an a crystalline form content at least equal to 95%, a water content at most equal to 1%, a compressibility, determined according to test A, at least equal to 80 N, said test A consisting in measuring the strength, expressed in Newton, which is necessary to cause a tablet prepared from said dextrose to be crushed, this strength thus reflecting the resistance to crushing of said tablet, which is cylindrical with convex sides (radius of curvature 14 mm), having a diameter of 13 mm, a thickness of 6 mm and a weight of 0.764 g, i.e. an apparent density of 1.3 g/ml, the said strength being exerted against the peripheral surface of the tablet in the direction of the axis of revolution thereof by means of a mechanical movable stop applied against the said surface along a generatrix, the said tablet being furthermore immobilized against the mechanical stationary stop also applied against the peripheral surface of the tablet along a generatrix, the latter being diametrically opposed to the generatrix against which the mechanical movable stop is applied.

* * * * *